(12) United States Patent
Sheehan et al.

(10) Patent No.: US 10,327,463 B2
(45) Date of Patent: *Jun. 25, 2019

(54) COMPOSITION AND METHODS TO CONTROL THE OUTGROWTH OF PATHOGENS AND SPOILAGE MICROORGANISMS IN HIGH MOISTURE AND LOW SODIUM SYSTEMS

(71) Applicant: Kerry Luxembourg S.à.r.l., Luxembourg (LU)

(72) Inventors: Vivien Sheehan, Roscoe, IL (US); Yiqing Cheng, Luxembourg (LU); Renetta Cooper, Elkhorn, WI (US); Eileen O'Shea, Luxembourg (LU); Jennifer Klatt, Luxembourg (LU); Beth Jones, Rochester, MN (US); Amara Venkata Sunil Perumalla, Janesville, WI (US)

(73) Assignee: Kerry Luxembourg S.à.r.l., Luxembourg (LU)

(*) Notice: Subject to any disclaimer, the term of this patent is extended or adjusted under 35 U.S.C. 154(b) by 0 days.

This patent is subject to a terminal disclaimer.

(21) Appl. No.: 15/788,621

(22) Filed: Oct. 19, 2017

(65) Prior Publication Data
US 2018/0035697 A1 Feb. 8, 2018

Related U.S. Application Data

(63) Continuation-in-part of application No. 15/097,922, filed on Apr. 13, 2016, now Pat. No. 9,883,689.

(60) Provisional application No. 62/149,365, filed on Apr. 17, 2015.

(51) Int. Cl.
| | |
|---|---|
| *A23B 4/12* | (2006.01) |
| *A23B 4/20* | (2006.01) |
| *A23L 3/3571* | (2006.01) |
| *A01N 37/46* | (2006.01) |
| *A01N 43/90* | (2006.01) |
| *A01N 63/02* | (2006.01) |
| *A23B 4/24* | (2006.01) |
| *A23B 7/155* | (2006.01) |
| *A23L 2/44* | (2006.01) |
| *A23L 3/3508* | (2006.01) |
| *A23L 3/358* | (2006.01) |
| *A23B 4/22* | (2006.01) |
| *A23L 3/3463* | (2006.01) |
| *A23K 20/105* | (2016.01) |
| *A23K 20/147* | (2016.01) |
| *A23K 20/195* | (2016.01) |
| *A23K 30/00* | (2016.01) |

(52) U.S. Cl.
CPC ............ *A23L 3/3571* (2013.01); *A01N 37/46* (2013.01); *A01N 43/90* (2013.01); *A01N 63/02* (2013.01); *A23B 4/12* (2013.01); *A23B 4/20* (2013.01); *A23B 4/22* (2013.01); *A23B 4/24* (2013.01); *A23B 7/155* (2013.01); *A23K 20/105* (2016.05); *A23K 20/147* (2016.05); *A23K 20/195* (2016.05); *A23L 2/44* (2013.01); *A23L 3/34635* (2013.01); *A23L 3/358* (2013.01); *A23L 3/3508* (2013.01); *A23K 30/00* (2016.05)

(58) Field of Classification Search
CPC ......................... A23B 4/12; A23B 4/20; A23L 3/3463; A23L 3/3465; A23L 3/34635
See application file for complete search history.

(56) References Cited

U.S. PATENT DOCUMENTS

| | | |
|---|---|---|
| 5,217,950 A | 6/1993 | Blackburn et al. |
| 5,219,603 A | 6/1993 | Boudreaux et al. |
| 5,573,797 A | 11/1996 | Wilhoit |
| 5,573,801 A | 11/1996 | Wilhoit |
| 6,207,411 B1 | 3/2001 | Ross et al. |
| 6,509,050 B1 | 1/2003 | Henson et al. |
| 7,001,632 B2 | 2/2006 | Nauth et al. |
| 9,883,689 B2 * | 2/2018 | Perumalla ............ A23K 30/00 |
| 2003/0108648 A1 | 6/2003 | Ming et al. |
| 2006/0229244 A1 | 10/2006 | Dorit et al. |
| 2011/0053832 A1 | 3/2011 | Antoniewski et al. |
| 2013/0012428 A1 | 1/2013 | Jacobus et al. |
| 2015/0140186 A1 | 5/2015 | Sliekers et al. |
| 2016/0302456 A1 * | 10/2016 | Perumalla ............ A23K 30/00 |

FOREIGN PATENT DOCUMENTS

EP 0 384 319 A1 8/1990

OTHER PUBLICATIONS

International Search Report dated Jul. 19, 2016 from the International Searching Authority in counterpart International Application No. PCT/US2016/027520.
Written Opinion of the International Seraching Authority dated Jul. 19, 2016 in counterpart International Application No. PCT/US2016/027520.
Desmond, E.; Reducing salt: A challenge for the meat industry, Meat Science, 74 (2006), pp. 188-196.
Bouvard, et al.; On behalf of the International Agency for Research on Cancer Monograph Working Group, The Carcinogenicity of consumption of red and processed meat. The Lancet Oncology. Published Online: Oct. 26, 2015; 3 pages.
Hustad, G. O et al.; Effect of sodium nitrite and sodium nitrate on botulinal toxin production and nitrosamine formation in wieners. Appl. Microbiology, Jul. 1973, p. 22-26, vol. 26, No. 1.

(Continued)

*Primary Examiner* — Jeffrey E. Russel
(74) *Attorney, Agent, or Firm* — Sughrue Mion, PLLC

(57) ABSTRACT

A method of inhibiting the outgrowth of pathogens and spoilage microorganisms in food and beverage products having a moisture content of about 38-80% by weight, a salt content of less than about 5.0% by weight, and a pH range of about 4.6 to about 8.5. The application of an organic acid or its salt with a fermentation derived antimicrobial peptide offers a robust solution to curtail growth of spores and vegetative cells without the need for chemicals, such as sodium nitrite, sodium nitrate or sorbate.

16 Claims, 5 Drawing Sheets

(56) References Cited

OTHER PUBLICATIONS

Schlyter, J.H.; The effects of diacetate with nitrite, lactate, or pediocin on the viability of Listeria monocytogenes in turkey slurries. International Journal of Food Microbiology, 19 (1993) 271-281.

Jozala, A.F. et al.; Processing of byproducts to improve nisin production by Lactococcus lactis; African Journal of Biotechnology, vol. 10(66), pp. 4920-14925, Oct. 24, 2011.

Farber, J. et al.; Modelling the effects of various parameters on the growth of Listeria monocytogenes on liver pate. Food Microbiology, 1995, 12, 447-453.

Santarelli, R. L. et al.; Processed meat and colorectal cancer: a review of epidemiologic and experimental evidence. Nutrition and Cancer, 60(2), 131-144., 2008.

Juneja, V. K. et al.: Inhibitory effects of organic acid salts on growth of Clostridium perfringens from spore inocula during chilling of marinated ground turkey breast. International Journal of Food Microbiology, 93 (2004) :155-163.

USDA; Scientific Report of the 2015 Dietary Guidelines Advisory Committee, Advisory Report of the Secretary of Health and Human Services and the Secretary of the Agriculture; Feb. 2015; 571 pages.

\* cited by examiner

US 10,327,463 B2

COMPOSITION AND METHODS TO CONTROL THE OUTGROWTH OF PATHOGENS AND SPOILAGE MICROORGANISMS IN HIGH MOISTURE AND LOW SODIUM SYSTEMS

CROSS REFERENCE TO RELATED APPLICATIONS

This patent application is a continuation-in-part of application Ser. No. 15/097,922, filed Apr. 13, 2016, which claims the benefit of U.S. Provisional Patent Application No. 62/149,365, filed Apr. 17, 2015. The entire teachings and disclosures of both application are incorporated herein by reference in their entireties.

FIELD OF THE INVENTION

This invention generally relates to composition and methods to inhibit pathogens and spoilage microorganisms.

BACKGROUND OF THE INVENTION

An increasing number of consumers believe foods that are free of synthetic or chemical additives are healthier. In response to these consumer trends and preferences, the food industry has focused efforts on offering various alternatives such as clean label and/or natural products that are free from artificial preservatives while retaining similar microbial safety characteristics as compared to conventionally prepared products.

Curing agents such as salts of sodium nitrate and sodium nitrite ("cured") have a long history of preserving the microbial safety of processed meat formulations as they provide functional benefits of antimicrobial and antioxidant activities in addition to delivering desirable color and flavor attributes characteristic of such products (See e.g. Pegg, R. B., and F. Shahidi. 2000. Nitrite curing of meat: the N-nitrosamine problem and nitrite alternatives. Food & Nutrition Press, Inc., Trumbull, Conn., incorporated by reference herein in its entirety).

However, the consumption of processed meats formulated with such curing agents has recently been linked with an increased risk of colorectal cancer due to the formation of cancer causing N-nitroso compounds and poly cyclic aromatic hydrocarbons (See e.g. Santarelli, R. L., Pierre, F., & Corpet, D. E. 2008. Processed meat and colorectal cancer: a review of epidemiologic and experimental evidence. Nutrition and Cancer, 60(2), 131-144., incorporated by reference herein in its entirety). Moreover, the International Agency for Research on Cancer (IARC, a subsidiary of WHO) and American Institute of Cancer Research (AICR) recently classified processed meats as Group 1 carcinogenic agents to humans (See e.g. Bouvard, et al. 2015, on behalf of the International Agency for Research on Cancer Monograph Working Group, The Carcinogenicity of consumption of red and processed meat. The Lancet Oncology. Published Online: 26 Oct. 2015, incorporated by reference herein in its entirety).

Meat products prepared without a curing agent either from synthetic or naturally occurring sources ("uncured" or "nitrate or nitrite free") are more susceptible to the growth of pathogens. Listeria monocytogenes and Clostridium species are two pathogens that are of particular concern in "uncured" or "nitrate or nitrite-free" products. Listeria monocytogenes is a psychrotroph that can grow even at refrigeration temperatures and thus pose food safety risk in extended shelf life ready to eat (RTE) meat and poultry products. Spore forming enterotoxigenic species of Clostridia such as Clostridium botulinum and Clostridium perfringens associated with processed meat and poultry are also of particular concern. While the heat applied in manufacturing RTE processed meat products is sufficient to inhibit vegetative cells, spores will not be inactivated but rather may germinate and develop into vegetative cells.

Spoilage organisms also play an important role in reducing the shelf-life of both raw (fresh) and uncured RTE refrigerated meat and poultry. For example, species of Pseudomonas and Lactobacillus are predominantly responsible for undesirable defects such as off-flavors, discoloration, gas and slime etc.

Additionally, in recent times there has been a movement to reduce the sodium content in food (See e.g. Scientific Report of the 2015 Dietary Guidelines Advisory Committee. Advisory Report of the Secretary of Health and Human Services and the Secretary of the Agriculture). Sodium is an effective preservative and its reduction makes formulations more vulnerable to a higher risk of pathogen and spoilage growth and thus results in shorter product shelf life (See e.g. Desmond, E. 2006. Reducing salt: A challenge for the meat industry, Meat Science, 74 (2006), pp. 188-196, incorporated by reference herein in its entirety).

In cured products, low levels of sodium nitrite, approx. 50 ppm, are sufficient for the inhibition of Clostridium species in processed meat formulations (See e.g. Hustad, G. O., J. G. Cerveny, H. Trenk, R. H. Deibel, D. A. Kautter, T. Fazio, R. W. Johnston, and O. E. Kolari. 1973. Effect of sodium nitrite and sodium nitrate on botulinal toxin production and nitrosamine formation in wieners. Appl. Microbiol. 26:22-26. incorporated by reference herein in its entirety).

Nevertheless, the maximum allowed level of 156 ppm sodium nitrite when used without the addition of adjunct antimicrobials is insufficient for the inhibition of Listeria monocytogenes (See e.g. Farber, J. M., R. C. McKellar, and W. H. Ross. 1995. Modelling the effects of various parameters on the growth of Listeria monocytogenes on liver pate. Food Microbiol. 12:447-453, incorporated by reference herein in its entirety).

Similar or comparable results are expected in inhibition of Listeria and Clostridia sps. when alternative sources of nitrate or nitrite (derived either by synthetic or fermentation methods) used to deliver similar concentrations equivalent to sodium nitrite as described in the examples listed above.

Previous studies have investigated organic acids or their salts for the inhibition of these pathogens in RTE processed meat applications. In particular, studies suggest that acetic acid or its salt alone when used at concentrations (<1%) that are expected to provide acceptable sensory attributes in RTE meat and poultry products, failed to inhibit C. perfringens in turkey breast meat (See e.g. Juneja, V. K., and H. Thippareddi. 2004. Inhibitory effects of organic acid salts on growth of Clostridium perfringens from spore inocula during chilling of marinated ground turkey breast. Int. J. Food Microbiol. 93:155-163, incorporated by reference herein in its entirety).

Additional studies demonstrated that 0.3-0.5% sodium diacetate when used alone or in combination with additional antimicrobials were effective in controlling Listeria monocytogenes in turkey slurries formulated with and without sodium nitrite (See e.g. Schlyter, J. H., Glass, K. A., Loeffelholz, J., Degnan, A. J., Luchansky, J. B., 1993. The effects of diacetate with nitrite, lactate, or pediocin on the viability of Listeria monocytogenes in turkey slurries. Int. J. Food Microbiol. 19, 271-281, incorporated by reference herein in its entirety). However, the suggested levels were higher than the maximum allowed levels (0.25% of the product formulation; FSIS 7120 list) in meat and poultry products in the U.S. and is expected to contribute an unacceptable flavor to the finished product. Additionally, other attempts have demonstrated the use of propionic acid or its salt in combination with pediocin to control *Listeria monocytogenes*. Nevertheless, to date known methods have failed to address control of *Clostridia* species, one of the predominant pathogen risks in uncured meat and poultry products.

While it is known to utilize nisin in combination with organic acids, the efficacy of these systems required emulsifiers and were dependent on the sequential addition of these individual components. In addition, these compositions did not demonstrate efficacy to inhibit pathogens and spoilage microorganisms of concern under the conditions specified herein. See, e.g., U.S. Patent Application Publication no. 2013/0012428 A1 to Jacobus et al.; incorporated by reference herein in its entirety.

U.S. Pat. No. 6,509,050 B1 to Henson et al., which is incorporated by reference herein in its entirety, demonstrated the use of polyphosphates in combination with an organic acid or its salts in controlling *Listeria monocytogenes* in a broth model and spoilage microorganisms in a cured meat system. As is known in the art, phosphates are typically used in meat applications to retain moisture and to improve the yield. However, there was no evidence of the efficacy of this approach for the inhibition of pathogens in a low sodium uncured meat system. Moreover, the levels of phosphates described therein are higher than currently allowed in the U.S. (0.5%; FSIS 7120 list).

To date, the simultaneous inhibition of *Listeria* and *Clostridia* species in RTE refrigerated meats formulated without sodium nitrite has not been reported. It is desirable to have a method that can demonstrate efficacy against foodborne pathogens and spoilage microorganisms in an "uncured" or "nitrite-free" system & with acceptable flavor that have a moisture content of about 38-80% by weight, a salt content less than about 5% by weight, and in a pH range of about 4.6-8.5.

Therefore, the cumulative effects of replacing chemical preservatives with clean label options in addition to lowering the sodium levels in foods has obligated food manufacturers to compromise shelf life. While there are several ways (methods and antimicrobials) to control the foodborne pathogens and spoilage in traditional processed meat and poultry products formulated using sodium nitrite, there is a need in the art for methods to eliminate such compromise and enhance the safety of clean label products formulated without sodium nitrite (uncured or sodium nitrite-free). It is also preferred to demonstrate a method of inhibiting the pathogens and spoilage microorganisms with one solution that has broad antimicrobial properties in diverse matrices and applications.

The current invention provides such a method of inhibition. These and other advantages of the invention, as well as additional inventive features, will be apparent from the description of the invention provided herein.

BRIEF SUMMARY OF THE INVENTION

The invention described herein relates to a method of inhibiting the growth of pathogens and spoilage organisms in a medium having a moisture content of about 38-80% by weight, a salt content of less than about 5.0% by weight, and a pH range of about 4.6-8.5, by the application of an effective amount of an antimicrobial composition and offers a robust alternative to conventional preservatives. The antimicrobial composition comprises an organic acid or its salt and a fermentation derived antimicrobial peptide and is free of any emulsifying and or chelating agents. The antimicrobial composition can be applied at all stages of processing, including but not limited to pre-mixing and pre-cooking when applied to processed foods. It can also applied by spraying, direct addition, injection, pumping tumbling, massaging etc.

The proposed method can suppress the growth of pathogens and spoilage microorganisms in systems, including, but not limited to, cheese, bread, meat and poultry, beverages, as well as cleaning agents, animal feedstuffs, cosmetics, and pharmaceuticals.

The organic acid is selected from acetic, citric or propionic acid, or the salt thereof, alone or in combinations thereof. The organic acids can be naturally derived (as one example, vinegar) or chemically synthesized. By a salt of an organic acid, it is meant generally a monovalent or divalent metal salt of the organic acid including but not limited to sodium, potassium, calcium and magnesium salt of the organic acid.

The fermentation derived antimicrobial is comprised of a bacteriocin or its analogues or derivatives, whereby the bacteriocin is a ribosomally synthesized antimicrobial peptide produced by certain bacteria which kill or inhibit the growth of closely related bacteria. The peptide can be any form either synthetic or derived from fermentation. As defined herein, bacteriocin analogues or derivatives include bacteriocins that differ from each other by as few as one and up to ten amino acids. By way of example, see O'Connor et al, Appl. Environ. Microbiol 2015 vol. 81 no. 12, pp. 3953-3960 and Rouse et al., Microbial Biotechnology 2012 5(4), pp. 501-508, both incorporated by reference herein in their entireties, which disclose exemplary analogues and derivatives of bacteriocins, some of which differ by only one amino acid, including nisin A, nisin Z, nisin F, nisin Q, nisin U, nisin U2, nisin P, and nisin H.

This antimicrobial intervention applies to food and non-food systems and includes various packaging conditions, such as vacuum, non-vacuum, and modified atmospheric conditions.

In one exemplary embodiment of the invention, an antimicrobial composition to control the outgrowth of pathogens and spoilage microorganisms in food or beverage products having a moisture content of about 38% by weight to about 80% by weight, a salt content of less than about 5.0% by weight, and having a pH range of about 4.6 to about 8.5 is provided. The composition includes an organic acid or its salt and fermentation derived antimicrobial peptide. The aforementioned pathogens may be species of *Listeria*, *Staphylococci*, and/or may be species of a class of spore formers comprising species of *Clostridia* or *Bacilli*. The spoilage microorganisms may include, for example, yeast or mold or species of *Lactobacilli*, *Leuconostoc*, *Pseudomonas*, *Brochothrix*, *Penicillium*, *Eurotium*, *Aspergillus*, *Saccharomyces* and *Zygosaccharomyces*.

The food and beverage products include, for example, cheese, bread, animal meat, beverages (soup) feed stuffs, or agricultural produce. The packaging conditions of the food or beverage products may be one of vacuum, non-vacuum and modified atmospheric conditions.

In a subsidiary embodiment according to this aspect, the organic acid includes acetic acid, lactic acid, propionic acid, citric acid, or a salt thereof, alone or in combinations thereof. The organic acids can be naturally derived (as one example, vinegar) or chemically synthesized.

In another subsidiary embodiment according to this aspect, the fermentation derived antimicrobial is a bacteriocin. The bacteriocin is a ribosomally synthesized antimicrobial peptide produced by certain bacteria which kills or inhibits the growth of closely related bacteria, for example, nisin, sakacin, pediocin, lactocin, and derivatives or analogues thereof. The peptide can be any form either synthetic or derived from fermentation. As one specific non-limiting example, the bacteriocin is nisin in an amount greater than about 1 ppm. The pH of nisin is from about 3.0 to about 6.5.

Preferably, the ratio of nisin to acetic acid or its salt is from 1 part nisin:2,750 parts acetic acid to 1 part nisin:40 parts acetic acid. In one embodiment, the disclosed antimicrobial composition can include at least about 1 part nisin to at least 2,750 parts acetic acid (for example, 1 ppm nisin: 2,750 ppm acetic acid). In another embodiment, the composition includes about 1 part nisin to about 183 parts acetic acid (for example 30 ppm nisin:5,500 ppm acetic acid). In yet another embodiment, the composition includes 1 part nisin to 110 parts acetic acid (for example, 50 ppm nisin:5, 500 ppm acetic acid).

Preferably, the ratio of nisin to propionic acid or its salt is from 1 part nisin:48 parts propionic acid to 1 part nisin:12 parts propionic acid. In one embodiment, the disclosed antimicrobial composition can include at least about 1 part nisin to at least 48 parts propionic acid (for example, 6.25 ppm nisin:300 ppm propionic acid). In another embodiment, the composition includes about 1 part nisin to about 12 parts propionic acid (for example, 50 ppm nisin: 600 ppm propionic acid).

Embodiments of the invention also include antimicrobial systems of a food or beverage product combined with antimicrobial compositions of an organic acid and a fermentation derived antimicrobial. In one embodiment, the antimicrobial composition includes a combination of acetic acid or its salt in a concentration of at least about 0.275% of the food or beverage product and nisin in a concentration of at least 1 ppm of the food or beverage product. In another embodiment, the antimicrobial composition includes at least about 300 ppm propionic acid or its salt by weight combined with at least about 6.25 ppm nisin by weight. In another embodiment, the antimicrobial composition includes about 1,200 ppm propionic acid in combination with about 100 ppm nisin by weight. In yet another embodiment, the antimicrobial composition includes about 600 ppm propionic acid or its salt by weight combined with about 50 ppm nisin by weight.

In another subsidiary aspect according to this invention, an antimicrobial activity of the composition is bacteriostatic or bacteriocidal. The composition may be in powder or liquid format. When in solution, the composition has a pH from about 4 to about 8.

In another exemplary embodiment of the invention, a method for controlling the outgrowth of pathogens and spoilage microorganisms in food or beverage products is provided. The method includes providing a food or beverage product having a moisture content of about 38% by weight to about 80% by weight, pH in the range of about 4.6 to about 8.5, and salt content less than about 5.0% by weight, in other embodiments a salt content less than about 3.0% by weight. The method also includes contacting the food or beverage product with an antimicrobial composition comprising an organic acid or its salt and a fermentation derived antimicrobial peptide to control growth of pathogens and growth of spoilage microorganisms.

In a subsidiary embodiment, the step of providing the food or beverage product includes providing a food or beverage product that is free of nitrate and nitrite that is derived either from synthetic or fermentation process. The pathogens include species of *Listeria* and *Staphylococci*. The pathogens also include species of a class of spore formers, including species of *Clostridia* and *Bacilli*. The spoilage microorganisms include, but are not limited to species of *Lactobacilli, Leuconostoc, Pseudomonas, Brochothrix, Penicillium, Eurotium, Aspergillus, Saccharomyces* and *Zygosaccharomyces*.

The food or beverage product include, but are not limited to cheese, bread, animal meat, beverages, feed stuffs, or agricultural produce. Some examples of food products of interest include processed cheeses, milk beverages and other dairy products, raw meats and processed meats, refrigerated or shelf stable meat snacks, non-meat snacks, meat substitutes such as tofu-based products, and processed meal kits. Additional examples include beverage syrups, ready to drink beverage products such as iced coffee, milk coffee, and vegetable based protein milks, for example, soy milk, coconut milk, almond milk. Other products of interest include egg-based ingredients such as liquid egg products. Also included in this category are bakery products, soups, meals, side dishes and sauces. The packaging conditions of the food or beverage products include vacuum, non-vacuum and modified atmospheric conditions.

In yet another exemplary embodiment, the invention provides an antimicrobial system comprising a food or beverage product comprising the following conditions: 1) a moisture content of about 38% by weight to about 80% by weight, 2) pH in the range of about 4.6 to about 8.5, and 3) a salt content of less than about 5.0% by weight and in certain embodiments a salt content of less than about 3% by weight, the system also including an organic acid or its salt, a fermentation derived peptide, wherein, the organic acid or its salt and the fermentation derived peptide are applied to control microbial growth the food or beverage product at said conditions.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

Figure 1:
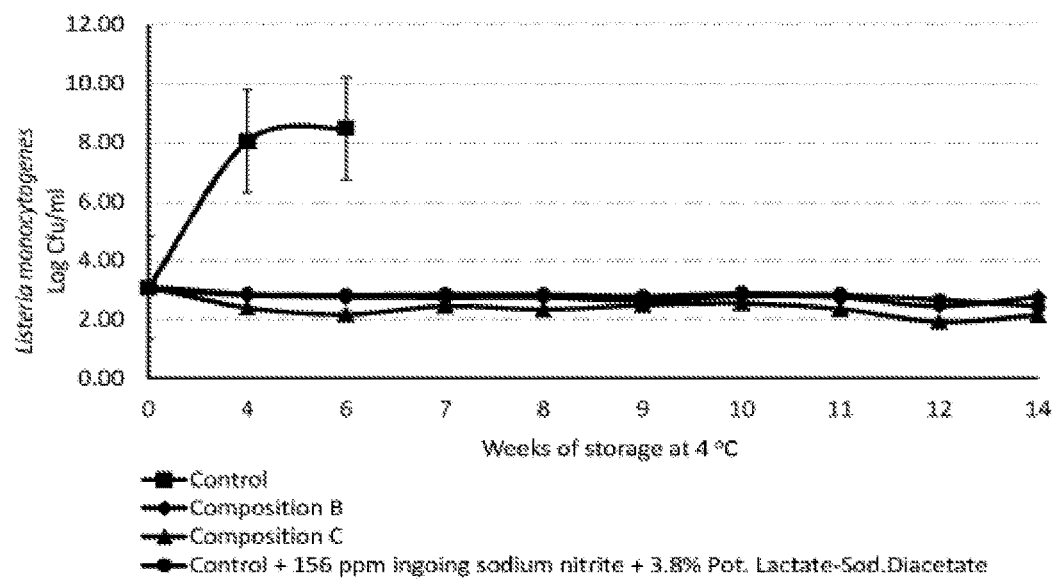
FIG. 1 illustrates the inhibition of *L. monocytogenes* outgrowth on surface inoculated uncured deli-style turkey slices stored in vacuum packaging at 4° C. for 14 weeks.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Food products containing a high moisture content are more favorable substrates for the outgrowth of pathogens and spoilage bacteria and therefore should be formulated with efficient antimicrobial(s) to minimize the public health risks as well as economic losses to the processors. Some examples of food products include processed cheeses, milk beverages and other dairy products, raw meats and processed meats, refrigerated or shelf stable meat snacks, non-meat snacks, meat substitutes such as tofu-based products, and processed meal kits. Additional examples include beverage syrups, ready to drink beverage products such as iced coffee, milk coffee, and vegetable based protein milks, for example, soy milk, coconut milk, almond milk. Other products include egg-based ingredients such as liquid egg products. Also included in this category are bakery products, soups, meals, side dishes and sauces.

The antimicrobial formulation in the methods described are comprised of an organic acid or its salt and an antimicrobial peptide, whereby the organic acid in one embodiment is acetic acid at an inclusion level of at least about 0.275% by weight, and the antimicrobial peptide is nisin, used at a quantity to deliver activity in the range of about 1-50 ppm, preferably about 7-30 ppm.

In another embodiment, the organic acid is propionic acid at an inclusion level of at least about 300 ppm by weight, and the antimicrobial peptide is nisin, used at a quantity to deliver activity in the amount of at least about 6.25 ppm. In another embodiment, propionic acid is included at an inclusion level of about 1,200 ppm by weight, and nisin is used at a quantity to deliver activity in the amount of about 100 ppm. In yet another embodiment, propionic acid is include at an inclusion level of about 600 ppm, and nisin is used at a quantity to deliver activity in the amount of about 50 ppm.

In addition to delaying the toxin production of spore formers, the antimicrobial composition is bacteriostatic and in some cases bactericidal for controlling vegetative pathogens as well as spoilage bacteria. Consequently, it can enhance the product safety and extend shelf life. By way of example, the inventors have achieved a shelf life of 120 days at 4° C. through application of the disclosed antimicrobial formulations containing an organic acid at an inclusion level of at least 0.275% by weight and at least 1 ppm nisin. Shelf life is defined herein as the period of time during which a material may be stored and remain fit for purpose from a microbiological and organoleptic perspective.

For example, demonstrating no more than 2 log or preferably no more than 1 log outgrowth and even more preferably 0 log outgrowth of a pathogen throughout 120 days has been found to satisfy shelf life requirements. Additionally, total plate counts less than 1,000,000 cfu/g at the end of shelf life throughout the 120 days likewise satisfies shelf life requirements. For example, in one experiment, 2-log of *Listeria* was inoculated into meat and was held at 4° C. for 120 days. Success criteria with respect to the 120 day shelf life were dependent on demonstrating no more than 2 log or more preferably no more than 1 log outgrowth of *Listeria* throughout the shelf life. Additionally, total plate counts were also monitored and were confirmed to be less than 1,000,000 cfu/g at the end of shelf life.

Nisin levels required to achieve antimicrobial efficacy were calculated by performing a modification of the agar diffusion assay previously described with the use of *Pediococcus pentosaceus* FBB63 as the indicator strain (See e.g. Jozala, A. F., Silva, D. P., Vicente, A, A, Teixeira, J. A., Junior, A. P., and Penna, T. C. V. 2011. Processing of byproducts to improve nisin production by *Lactococcus lactis*. Afr. J Biotech 10:14920-14925) The activity of the fermentation derived nisin was compared with a commercially known standard sample of Nisaplin. A conversion factor thus derived [1 Arbitrary Unit (AU)/g=1.04×International Unit (IU)/g] was used in calculating the levels in part per million (ppm) required for the antimicrobial effects (1 ppm=40 IU).

Compositions comprising various ratios of each of the components within the preferred ranges outlined are referred to as compositions A-J going forward. In those compositions, reference to percent by weight means the percent by weight taking into account the food product which the compositions are introduced in.

Example 1—Methods to Inhibit *L. monocytogenes* Outgrowth in an Uncured Meat with High Moisture and Low Sodium in the System This embodiment describes the antimicrobial composition to control the outgrowth of pathogens such as *L. monocytogenes* in high moisture and reduced sodium systems, for example, a ready to eat uncured deli-style turkey product.

Uncured deli-style turkey (70% turkey breast, 25.6% water, 2% starch, 1% sugar, 1% salt, 0.4% sodium phosphate, 0% sodium nitrite) was prepared under Good Manufacturing Practices. Appropriate levels of antimicrobials for each treatment were added along with non-meat ingredients, stuffed in to chubs and cooked to a final temperature of 73.8° C. The moisture of the finished product compositions were in the range of 72%-76%, with reduced sodium levels of 350-450 mg per 56 g of serving and a pH value of 6.1-6.4.

The product was sliced (22-28 g/slice using a sanitized slicer to prevent contamination with spoilage microbes) and stored at 4° C. until use in the studies mentioned herein. Cooked slices were surface inoculated with 3 log CFU/g of a five-strain mixture of *L. monocytogenes* including strains FSL-C1-109 (serotype 4b), LM101M (4b), LM310 (4b), LM132 (½ a), and LM108M (½b), vacuum packed (100 g/package), and stored at 4° C. during the study. Populations of *L. monocytogenes* were enumerated from inoculated samples in triplicate. At each time point, inoculated treatments were homogenized in sterile Butterfield's buffer and plated on Modified Oxford agar (35° C., 48 h). Treatments that supported more than 2.0 log CFU/ml from day zero were deemed as spoiled and were discontinued from the study.

In a preferred embodiment, the application of the antimicrobial demonstrated the inhibition of *L. monocytogenes* growth over 14 weeks of storage at 4° C. Treatments included: (i) control without antimicrobials, (ii) composition B at 2.0% by weight, (iii) composition C at 2.7% by weight, and (iv) a control formulated with 156 ppm ingoing sodium nitrite and 3.8% potassium lactate-diacetate by weight, a blend that is typically used in the industry. The results are presented in FIG. 1.

Un-inoculated turkey deli slices were subjected to sensory evaluation to determine the overall acceptability as perceived by five trained panelists. Test samples were compared with a control which did not contain antimicrobials or sodium nitrite and were deemed acceptable by the panelists with descriptors that are similar to the control (salt, sweet, sour, turkey flavor).

Figure 2:
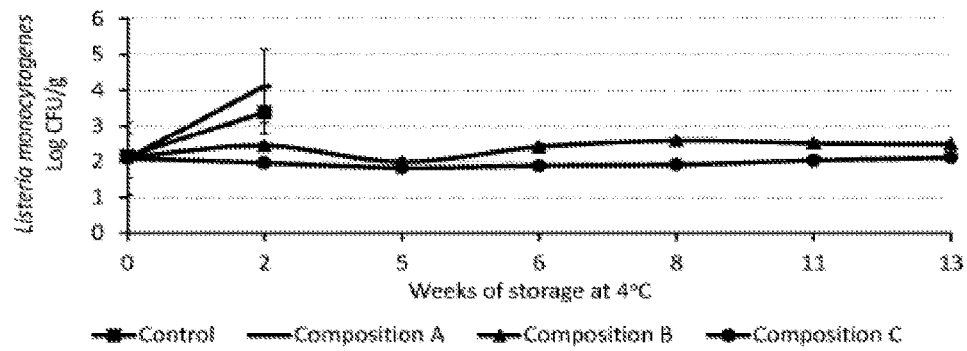
FIG. 2 illustrates the antimicrobial efficacy of the peptide component alone and in combination with organic acid or its salt against *L. monocytogenes* following surface inoculation on uncured deli-style turkey slices, under vacuum packaging conditions at 4° C. for 13 weeks.

In another preferred embodiment, buffered vinegar and antimicrobial peptide demonstrated greater efficacy than antimicrobial peptide alone in controlling the outgrowth of *L. monocytogenes* in uncured deli-style turkey slices, under vacuum packaging at 4° C. for 13 weeks. Treatments included: (i) control without antimicrobials, (ii) composition A at 1.2% by weight containing antimicrobial peptide alone, (iii) composition B at 3.2% by weight, and (iv) composition C at 3.9% by weight. The results are presented in FIG. 2.

Figure 3:
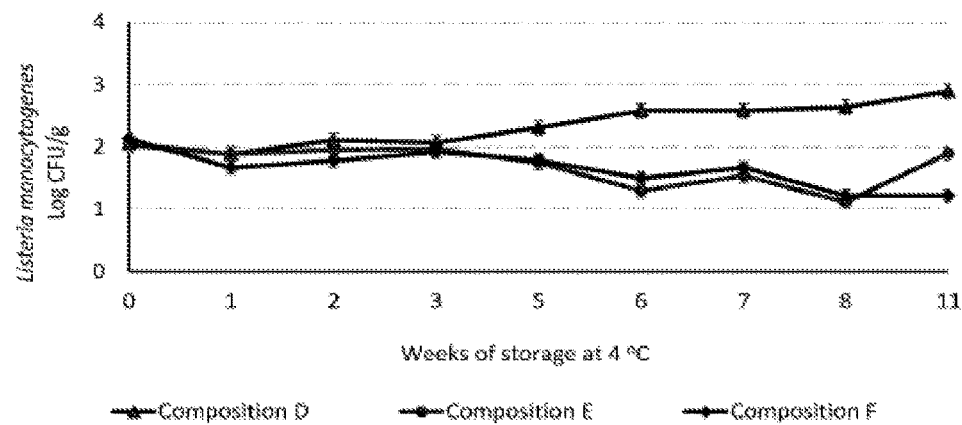
FIG. 3 illustrates the growth of *L. monocytogenes* on surface inoculated uncured deli-style turkey slices stored in non-vacuum packaging conditions at 4° C. for 11 weeks.

In another preferred embodiment, an uncured deli-style turkey formulation did not support the outgrowth of *L. monocytogenes* in slices packaged in non-vacuum conditions and stored at 4° C. for 11 weeks. Treatments included: (i) control without antimicrobials, (ii) composition D at 1.85% by weight, (iii) composition E at 2.95% by weight, and (iv) composition F at 3.15% by weight. The results are presented in FIG. 3.

Figure 4:
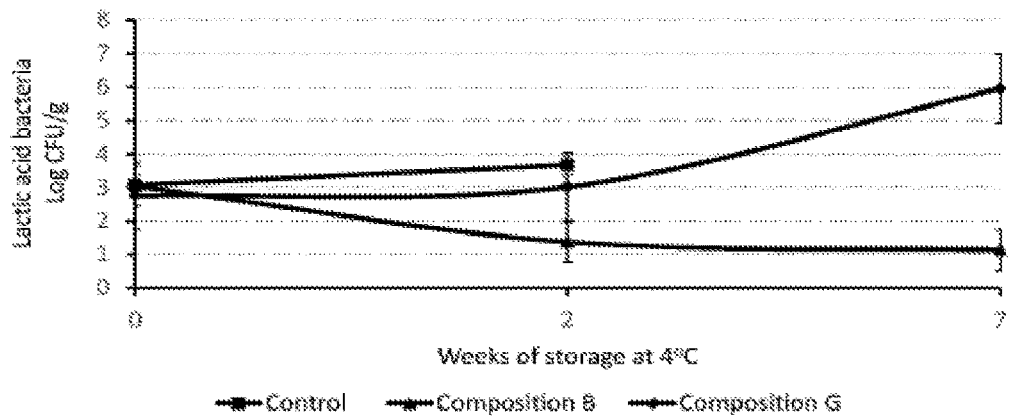
FIG. 4 illustrates the efficacy of the antimicrobial application against lactic acid bacteria in uncured deli-style turkey slices stored in vacuum packaging conditions at 4° C. for 7 weeks.

Example 2—Methods to Inhibit Spoilage Microorganisms Such as Lactic Acid Bacteria Growth in an Uncured Meat with High Moisture and Low Sodium in the System This embodiment describes the efficacy of the method of allying the antimicrobial composition for controlling spoilage bacteria especially lactic acid bacteria. This experiment was conducted in an uncured meat model with high moisture and low sodium conditions as described in example 1 and subjected to a shelf-life study at 4° C. for 7 weeks. Three formulations of the uncured deli-style turkey were prepared as per the recipe mentioned in example 1. Treatments included: (i) control without antimicrobials, (ii) composition B at 2.0% by weight, and (iii) composition G at 2.36% by weight. Initial counts of background microflora in the product post cooking described herein reflects the contamination scenario during the handling and slicing. Lactic acid bacteria plate counts were determined by plating in duplicate un-inoculated samples on APT agar with bromocresol purple indicator. Plates were incubated at 25° C. for 48 h. The results are presented in FIG. 4.

These results indicate that a combination of buffered vinegar and antimicrobial peptide is more effective in controlling the spoilage bacteria under the specific conditions challenged than a combination of lactic acid and antimicrobial peptide.

Example 3—Methods to Control the Growth of *Clostridium sporogenes*

Antimicrobial activity against *C. sporogenes* PA 3679 was demonstrated in a broth study using modified cooked meat medium as the former has proven to be an on-toxigenic surrogate for *C. botulinum*. Treatments included: (i) control without antimicrobials, (ii) composition B at 2.0% by weight, and (iii) composition C at 2.7% by weight. All the variables were inoculated with spores that had been heat shocked at 85° C. for 5 min at a target of 2.0 log CFU/g and incubated anaerobically at 25° C. for 3-4 days. Growth of *C. sporogenes* was monitored by plating appropriate dilutions on modified McLung's agar and incubation at 35-37° C. for 3 days. Each treatment was assayed in duplicate. The results are shown in Table 1.

TABLE 1

Method of inhibition of *C. sporogenes* by the antimicrobial composition in modified cooked meat medium at 25° C.

| Treatment | Initial Log CFU/ml (Time zero) | Final Log CFU/ml (After 72 hours) |
| --- | --- | --- |
| Control | 2.0 | 7.23 |
| Composition B 2.0% by weight | 2.0 | 0 |
| Composition C 2.7% by weight | 2.0 | 0 |

As will be easily appreciated by those of skill in the art based on the data presented in Table 1, the application of buffered vinegar in combination with antimicrobial peptide is effective in preventing the outgrowth of *C. sporogenes*.

Example 4—Methods of Inhibiting the Outgrowth of *L. monocytogenes* Growth in a Cured Meat Model (with Low Levels of Curing Agents than Traditional Usage Levels) with High Moisture and Low Sodium in the System This embodiment describes the method of using the antimicrobial composition to control the outgrowth of pathogens such as *L. monocytogenes* in a meat model formulated with the minimum amount of curing agent required for contributing color and flavor attributes in systems. For example, in commercial processed meat formulation, a maximum of 156 ppm of ingoing sodium nitrite is used in conjunction with an antimicrobial to achieve a typical shelf-life of 90 days at refrigerated storage. In a preferred embodiment, the level of ingoing sodium nitrite is significantly reduced to as low as 20 ppm sodium nitrite in combination with the antimicrobial composition described and achieved the same shelf-life extension.

Deli-style cured turkey product (70% turkey breast, 25.6% water, 2% starch, 1% sugar, 1% salt, and 0.4% sodium phosphate) was prepared under Good Manufacturing Practices. Appropriate levels of antimicrobials for each treatment were added along with non-meat ingredients, stuffed in to chubs and cooked to a final temperature of 73.8° C. The composition of the finished product was found to be high in moisture (76% moisture), reduced sodium (340 mg of sodium/56 g of serving) and at a nearly neutral pH (6.1-6.3). Cooked slices were inoculated, vacuum packed, and stored at 4° C. to evaluate the efficacy for the control of *L. monocytogenes* as described in example 1. Treatments included: (i) 80 ppm sodium nitrite by weight, (ii) 40 ppm sodium nitrite by weight+composition H at 2.0% by weight, and (iii) 20 ppm sodium nitrite by weight+composition I at 2.7% by weight. The results are presented in FIG. 5.

Un-inoculated turkey deli slices were subjected to sensory evaluation to determine the overall acceptability as perceived by five trained panelists. Samples were compared to a control sample containing 80 ppm ingoing sodium nitrite (by weight) without additional antimicrobials and were deemed as acceptable by the panelists with descriptors that were similar to the control (cured, savory, sweet, sour, turkey flavor).

Figure 5:
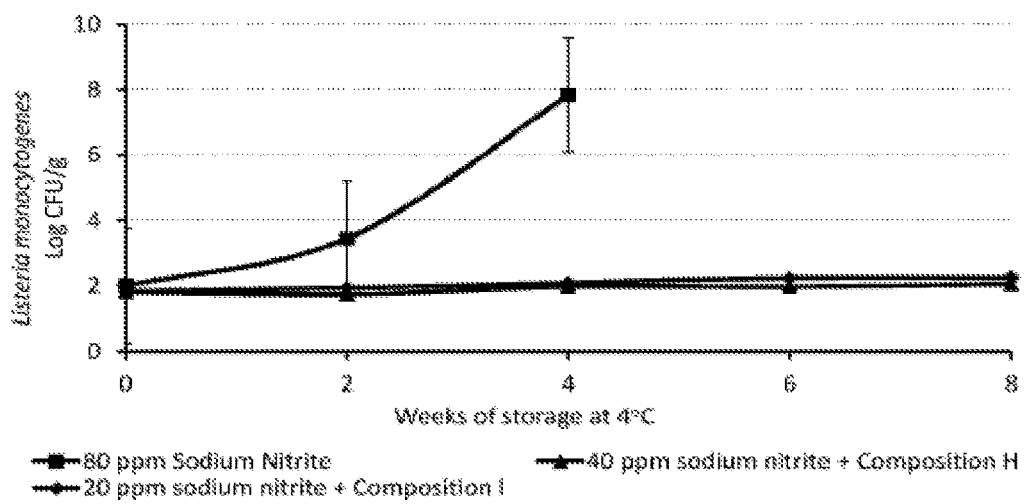
FIG. 5 illustrates the efficacy of antimicrobial application against *L. monocytogenes* following surface inoculation on cured deli-style turkey slice in vacuum packaging conditions at 4° C. for 8 weeks.

The results shown in FIG. 5 demonstrate that a blend of buffered vinegar and antimicrobial peptide in combination with cure (sodium nitrite) is more effective than cure alone. Furthermore, the antimicrobial composition has the potential to reduce the cure (sodium nitrite) levels in meat formulations without compromising the microbial quality.

Similar benefits are expected in inhibiting pathogens and spoilage organisms when sodium nitrates or nitrites either synthetic or natural source are used in the formulation.

Example 5: Method of Preventing or Delaying the Toxin Production by *Clostridium botulinum* in Uncured Chicken Batter This embodiment describes the method of preventing or delaying the toxin production by *Clostridium botulinum* in an inoculated uncured chicken meat batter (100 cfu/g). Uncured (sodium nitrite-free) chicken meat batter was prepared under Good Manufacturing Practices. The formulation was prepared with chicken meat (70%), water (23%), modified corn starch (2.1%), salt (1.5%), carrageenan (0.2%), and sodium phosphate (0.4%). Treatments included in this study (i) control without antimicrobials, (ii), composition B at 2.0% by weight, (iii) composition C at 2.7% by weight. Pre-grinded meat (⅛") was mixed with non-meat ingredients in a bowl chopper to prepare a meat batter, bagged, flattened, and kept frozen until use.

For testing, frozen batter is thawed and inoculated with *C. botulinum* spores which had been heat shocked at 80° C. for 10 min. Two individual batches of meat batter were inoculated with either proteolytic (33A, 36A, 62A, 77A, 53B, 113B, 213B, ACC1B) or non-proteolytic (K85, K86, K87, K88, K89) strains, cooked in bag using a water bath to an internal temperature of 73.8° C. The samples were cooled, and incubated for 2 days at 26.6° C. To examine toxin production, samples were pulled at 24 and 48 hours, extracts taken and administered to mice to verify the presence of toxin. Another batch of meat batter inoculated with non-proteolytic strains only was incubated for up to 8 weeks at 7° C. At weekly intervals, samples were taken, tryspsinized for toxin activation, and extracts were administered into mice for toxin bioassay.

Standard protocols were followed in growing and harvesting *Clostridia* cultures, and performing mouse toxin bioassay (see FDA Bacteriological Analytical Manual for Foods, chapter 17, 2015). Briefly, at each observation inoculated samples were weighed and an equal volume of gel-phopsphate buffer added (adjusting to pH 6.2), centrifuged under refrigeration to collect the aqueous supernatant fluid for toxin assay. This mixture was filtered through a millipore filter to avoid the nonspecific death of the mice. For non-proteolytic inoculated samples, trypsinization was performed after filtration to activate the toxin. The meat extract filtrate thus collected per each test sample at each observation point was diluted and administered (0.5 ml) to a pair of mice via intraperitoneal injection. Mice were observed for 48 hours and examined for symptoms and death characteristic of *C. botulinum* intoxication. Deaths following meat extract administration are presumptive evidence of toxin production. Further confirmation was achieved by challenging two additional mice with a pre-incubated (37° C. for 30 min.) antitoxin preparation (protected control). Death with nonspecific reasons such as chemicals present in injected fluid or trauma was dis-regarded and the challenge was repeated to confirm the toxin presence in the meat samples. The results of the study are shown in Tables 2 and 3. The results demonstrate that formulations prepared with the antimicrobial composition were effective in delaying the toxin formation in samples inoculated with a cocktail of proteolytic or non-proteolytic *C. botulinum* strains until 24 h of in incubation at 30° C. Furthermore, the antimicrobial compositions were also effective in delaying toxin formation in samples inoculated with non-proteolytic samples incubated for 9 weeks at 7° C.

TABLE 2

Presence of *Clostridium botulinum* toxin in uncured meat batters inoculated with proteolytic and non-proteolytic spore cocktails and incubated at 26.6° C. for 48 hours.

| Treatment | Inoculated with proteolytic cocktail and incubated for 48 hours. | | | | Inoculated with non-proteolytic cocktail and incubated for 48 hours. | | | |
| --- | --- | --- | --- | --- | --- | --- | --- | --- |
| | 0 hour | 24 hours | 36 hours | 48 hours | 0 hour | 24 hours | 36 hours | 48 hours |
| Control (No antimicrobials) | Negative | Positive | Positive | Positive | Negative | Positive | Positive | Positive |
| Composition B - 2.0% by weight | Negative | Negative | Positive | Positive | Negative | Negative | Positive | Positive |
| Composition C - 2.7% by weight | Negative | Negative | Negative | Positive | Negative | Negative | Positive | Positive |

TABLE 3

Presence of *Clostridium botulinum* toxin in uncured meat batters inoculated with non-proteolytic spore cocktails and incubated at 7° C. for 9 weeks.

| Treatment | Non-proteolytic cocktail incubated for 9 weeks. | | | | | | | | |
|---|---|---|---|---|---|---|---|---|---|
| | Week-1 | Week-2 | Week-3 | Week-4 | Week-5 | Week-6 | Week-7 | Week-8 | Week-9 |
| Control (No antimicrobials) | Negative | Negative | Negative | Positive | Positive | Not tested* | Not tested | Not tested | Not tested |
| Composition B - 2.0% by weight | Negative | Negative | Negative | Negative | Negative | Negative | Negative | Negative | Negative |
| Composition C - 2.7% by weight | Negative | Negative | Negative | Negative | Negative | Negative | Negative | Negative | Negative |

*Subsequent samples were not tested as results were positive in 2 prior consecutive time points.

Example 6: Efficacy of Antimicrobial Composition Against Spoilage Microorganisms in Fresh Chicken Breast Fillets Boneless, skinless, uncured chicken breast fillets were vacuum tumbled to achieve a target of 12% marinade pick-up based on the meat block. Marinated chicken breast fillets were stored in plastic bags (sealed without vacuum) at 4° C. until spoilage (≥6.0 log cfu/g). Samples were plated in duplicate on days 0, 7, 14, 21, 28, and 35. Twenty-five grams of sample was taken from each treatment bag under aseptic conditions and diluted (1:2) in 0.1% peptone water and homogenized for 1 min. Samples were plated on tryptic soy agar and *Pseudomonas* agar base. Treatments included: (i) control without antimicrobials, (ii) composition B at 2.0% by weight, and (iii) composition J at 1.6% by weight.

Figure 6:
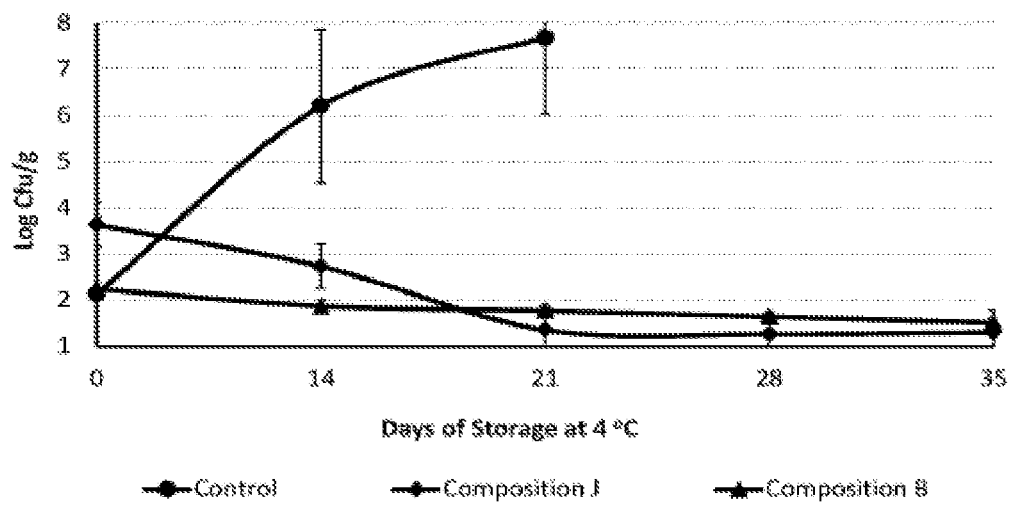
FIG. 6 illustrates the antimicrobial efficacy of the organic acid or its salt and antimicrobial peptide against spoilage microorganisms (total plate counts) in fresh chicken breast fillets at 4° C. for 35 days.
Figure 7:
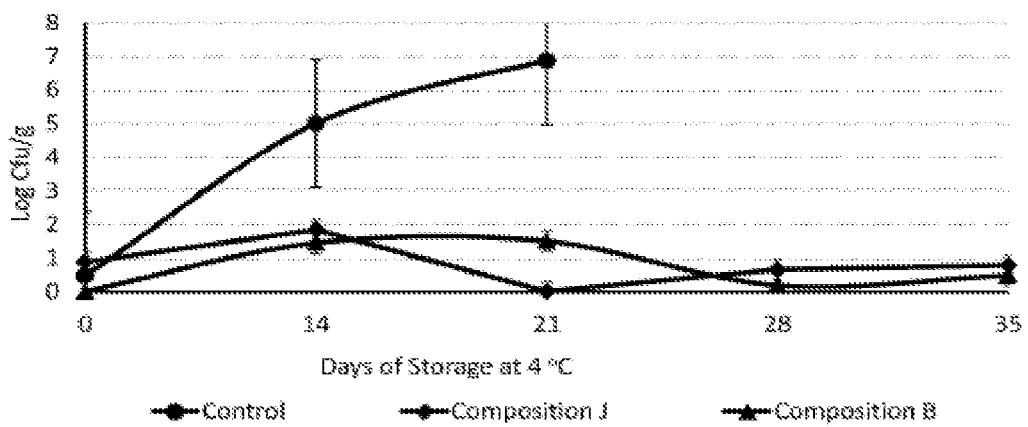
FIG. 7 illustrates the antimicrobial efficacy of the organic acid or its salt and antimicrobial peptide against the growth of *Pseudomonas* species in fresh chicken breast fillets at 4° C. for 35 days.

Results presented in FIGS. 6 and 7 demonstrate that marinated chicken breast fillets without antimicrobials spoiled by day 14 (total plate counts >6.0 log cfu/g), while the chicken breast fillets formulated with composition B (1.6% by weight) or J (2.0% by weight) extended the shelf life to 35 days at refrigerated storage.

Example 7—Inhibition of *Staphylococcus aureus* Outgrowth in a Broth Containing a Synergistic Combination of Propionic Acid and Nisin This embodiment describes the antimicrobial composition to control the outgrowth of pathogens such as *S. aureus* in a model system simulating the pH conditions encountered in processed cheese. Tryptic Soy Broth (TSB) (Becton, Dickinson and Company), whereby the pH was adjusted to 5.8 using 88% phosphoric acid, was used as the model system. Treatments included uninoculated samples and variables inoculated with *S. aureus*. Multiple propionic acid and nisin antimicrobial treatments were added to TSB with efficacy compared to TSB supplemented with sorbic acid. For each treatment, the broth was inoculated with 3.5-log of a 2-strain cocktail consisting of *S. aureus* ATCC 25923 and *S. aureus* 6538P. All treatments (uninoculated and inoculated with *S. aureus*) were stored at 27° C. for 22 hours after which the temperature was increased to 30° C. for a further 38 hours. The TSB samples were added to a 100 well microtiter plate which was placed in a bioscreen CTM automated microbiology growth curve analysis system (manufactured by Oy Growth Curves AB Ltd, Finland). The samples were measured at a wavelength of 600 nm every hour. Plates were incubated statically and automatically shaken for 5 seconds prior to measurement. Treatments included 12.5 ppm nisin, 2,400 ppm sorbic acid, 300 ppm propionic acid, 12.5 ppm nisin combined with 300 ppm propionic acid and 0.78 ppm nisin combined with 300 ppm propionic acid. Growth was determined by measuring the optical density (OD) at 1-hour intervals.

Figure 8:
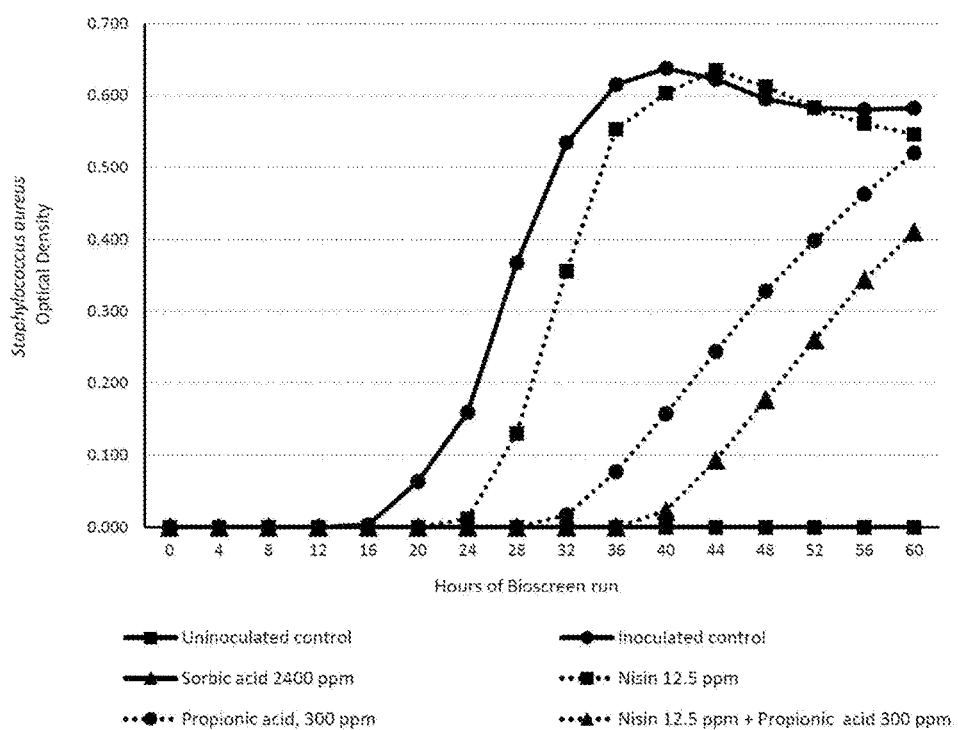
FIG. 8. illustrates optical density (OD) change of *Staphylococcus aureus* overtime in modified TSB (pH 5.8) formulated with and without antimicrobial treatments.

Results presented in FIG. 8 demonstrate that a synergistic effect inhibiting the outgrowth of *S. aureus* was observed when 12.5 ppm nisin was combined with 300 ppm propionic acid. The synergy is demonstrated by the lower concentration of each antimicrobial when used in combination in contrast to the higher concentrations when used alone. As further demonstrated, the antimicrobial compositions disclosed herein may be used as an effective alternative to sorbic acid in food and beverage products, such as processed cheese, to control outgrowth of *Staphylococcus aureus*.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A method using an antimicrobial composition to control the outgrowth of pathogens and spoilage microorganisms in food and beverage products, comprising the steps of:
providing a food or beverage product having a moisture content of about 38% by weight to about 80% by weight, pH in the range of about 4.6 to about 8.5, and salt content less than about 5.0% by weight;
contacting the food or beverage product with the antimicrobial composition comprising acetic acid or its salt and a fermentation derived antimicrobial peptide to control growth of pathogens and growth of spoilage microorganisms, wherein the acetic acid or its salt has a concentration in the food or beverage product of at least 0.275% by weight; and
packaging the food or beverage product.

2. The method of claim 1, wherein the food or beverage product is free of nitrate and nitrite that is derived from either synthetic or fermentation processes.

3. The method of claim 1, wherein the fermentation derived antimicrobial peptide comprises bacteriocins and antimicrobial peptides that differ from the bacteriocins by one to ten amino acids.

4. The method of claim 3, wherein the bacteriocin is selected from the group consisting of nisin, sakacin, pediocin, lactocin, and antimicrobial peptides that differ from the foregoing bacteriocins by one to ten amino acids.

5. The method of claim 4, wherein the bacteriocin is nisin at a concentration of at least about 1 ppm by weight in the food or beverage product.

6. The method of claim 1, wherein packaging conditions of the food or beverage products are one of vacuum and modified atmospheric conditions.

7. The method of claim 1, wherein packaging conditions of the food or beverage products are non-vacuum conditions.

8. The method of claim 1, wherein the food product is selected from the group consisting of cheese, bread, animal meat, feed stuffs, and agricultural produce.

9. An antimicrobial system comprising an antimicrobial composition and a food or beverage product,
said food or beverage product comprising the following conditions: 1) a moisture content of about 38% by weight to about 80% by weight, 2) pH in the range of about 4.6 to about 8.5, and 3) a salt content of less than about 5.0% by weight;
said antimicrobial composition comprising acetic acid or its salt at a concentration in the food or beverage product of at least 0.275% by weight and a fermentation derived antimicrobial peptide.

10. The antimicrobial system of claim 9, wherein the food product or beverage product is free of nitrate and nitrite that is derived from either synthetic or fermentation processes.

11. The antimicrobial system of claim 9, wherein the fermentation derived antimicrobial peptide is nisin at a concentration of at least about 1 ppm by weight in the food or beverage product.

12. The antimicrobial system of claim 9, wherein the antimicrobial system is free of sorbate.

13. The antimicrobial system of claim 9, wherein the antimicrobial system achieves a shelf life of at least 120 days at 4° C.

14. The method of claim 1, wherein the antimicrobial composition in solution has a pH from about 4.0 to about 8.0.

15. The method of claim 1, wherein the fermentation derived antimicrobial peptide is nisin, and wherein the nisin and the acetic acid or its salt are contained in the antimicrobial composition in a concentration ratio of from 1 ppm nisin:2,750 ppm acetic acid to 1 ppm nisin:40 ppm acetic acid.

16. The method of claim 1, wherein the pathogens comprise species of *Listeria, Staphylococci, Clostridia, Bacilli* and the spoilage microorganisms comprise yeast, mold, and species of Lactobacilli, *Leuconostoc, Pseudomonas, Brochothrix, Penicillium, Eurotium, Aspergillus, Saccharomyces* and *Zygosaccharomyces*.

* * * * *